United States Patent [19]
Pressman et al.

[11] Patent Number: 5,898,080
[45] Date of Patent: Apr. 27, 1999

[54] METHOD FOR PREPARING DIARYL CARBONATES EMPLOYING HEXAALKYLGUANIDINIUM HALIDES

[75] Inventors: Eric James Pressman, East Greenbush; Sheldon Jay Shafer, Clifton Park, both of N.Y.

[73] Assignee: General Electric Company, Schenectady, N.Y.

[21] Appl. No.: 09/040,264

[22] Filed: Aug. 27, 1997

Related U.S. Application Data

[60] Provisional application No. 60/040,300, Feb. 13, 1997.
[51] Int. Cl.$^6$ ..................................................... C07C 68/00
[52] U.S. Cl. .......................... 558/274; 558/271; 558/272; 558/273
[58] Field of Search .................................... 558/274, 271, 558/272, 273

[56] References Cited

U.S. PATENT DOCUMENTS 5,202,454 4/1993 Wooden et al. ..................... 558/271 X

*Primary Examiner*—Michael G. Ambrose
*Attorney, Agent, or Firm*—Noreen C. Johnson; Douglas E. Stoner

[57] ABSTRACT

Hydroxyaromatic compounds such as phenol are converted to diaryl carbonates by reaction with oxygen and carbon monoxide in the presence of a catalyst package which typically comprises a group VIIIB metal or compound thereof, an inorganic cocatalyst, an organic cocatalyst and a hexaalkylguanidinium bromide or chloride, preferably bromide. The use of the hexaalkylguanidinium salt causes an increase in the yield of diaryl carbonate without a decrease in selectivity.

17 Claims, No Drawings

METHOD FOR PREPARING DIARYL CARBONATES EMPLOYING HEXAALKYLGUANIDINIUM HALIDES

CROSS-REFERENCE TO RELATED APPLICATION

This application claims priority from provisional application Ser. No. 60/40,300, filed Feb. 13, 1997.

BACKGROUND OF THE INVENTION

This invention relates to the preparation of diaryl carbonates by carbonylation. More particularly, it relates to the improvement of diaryl carbonate yield in the carbonylation reaction.

Diaryl carbonates are valuable intermediates for the preparation of polycarbonates by transesterification with bisphenols in the melt. This method of polycarbonate preparation has environmental advantages over methods which employ phosgene, a toxic gas, as a reagent and environmentally detrimental chlorinated aliphatic hydrocarbons such as methylene chloride as solvents.

Various methods for the preparation of diaryl carbonates by a carbonylation reaction of hydroxyaromatic compounds with carbon monoxide and oxygen have been disclosed. In general, the carbonylation reaction requires a rather complex catalyst. Reference is made, for example, to U.S. Pat. No. 4,187,242, in which the catalyst is Group VIIIB metal, i.e., a metal selected from the group consisting of ruthenium, rhodium, palladium, osmium, iridium and platinum, or a complex thereof.

Further developments in the carbonylation reaction, including the use of such cocatalysts as cobalt pentadentate complexes and terpyridines, are disclosed in U.S. Pat. Nos. 5,231,210, 5,284,964 and 5,399,734. These patents also disclose the use of quaternary ammonium or phosphonium halides, as illustrated by tetra-n-butylammonium bromide, as part of the catalyst package.

The commercial viability of the carbonylation reaction would be greatly increased if product yield therein could be improved. The relatively low yields disclosed in the working examples of the above-identified patents include some in the single digits. It is evident, therefore, that methods to improve the yield are needed.

SUMMARY OF THE INVENTION

The present invention is based on the discovery that hexaalkylguanidinium halides are extremely active as halide sources for carbonylation. Their use in amounts essentially equivalent to the amounts of quaternary ammonium halides previously employed leads to a significant increase in product yield (i.e., percentage of hydroxyaromatic compound converted to reaction products) without a decrease in selectivity (i.e., the proportion of diaryl carbonate obtained as a percentage of all of said reaction products).

The invention, therefore, is a method for preparing a diaryl carbonate which comprises contacting at least one hydroxyaromatic compound with oxygen and carbon monoxide in the presence of an amount effective for carbonylation of at least one catalytic material including an effective proportion of a source of bromide or chloride, said source being at least one hexaalkylguanidinium bromide or chloride.

DETAILED DESCRIPTION; PREFERRED EMBODIMENTS

Any hydroxyaromatic compound may be employed in the present invention. Monohydroxyaromatic compounds, such as phenol, the cresols, the xylenols and p-cumylphenol, are generally preferred with phenol being most preferred. The invention may, however, also be employed with dihydroxyaromatic compounds such as resorcinol, hydroquinone and 2,2-bis(4-hydroxyphenyl)propane or "bisphenol A", whereupon the products are polycarbonates.

Other essential reagents in the method of this invention are oxygen and carbon monoxide, which react with the phenol to form the desired diaryl carbonate.

Any catalyst system effective in the carbonylation reaction may be employed. One essential catalyst constituent is one of the Group VIIIB metals, preferably palladium, or a compound thereof. Thus, palladium black or elemental palladium deposited on carbon are suitable, as well as palladium compounds such as halides, nitrates, carboxylates and complexes involving such compounds as carbon monoxide, amines, phosphines or olefins. Preferred in most instances are palladium(II) salts of organic acids, most often $C_{2-6}$ aliphatic carboxylic acids, and palladium(II) salts of β-diketones. Palladium(II) acetate and palladium(II) 2,4-pentanedionate are generally most preferred.

The catalyst package preferably also includes an inorganic cocatalyst of the type disclosed in the aforementioned U.S. Pat. No. 5,231,210 and/or an organic cocatalyst of the type disclosed in the aforementioned U.S. Pat. No. 5,284,964. It is preferred to employ both an inorganic and an organic cocatalyst.

Typical inorganic cocatalysts are complexes of cobalt(II) salts with organic compounds capable of forming complexes, especially pentadentate complexes, therewith. Illustrative organic compounds of this type are nitrogen-heterocyclic compounds including pyridines, bipyridines, terpyridines, quinolines, isoquinolines and biquinolines; aliphatic polyamines such as ethylenediamine and tetraalkyl-ethylenediamines; crown ethers; aromatic or aliphatic amine ethers such as cryptanes; and Schiff bases. The especially preferred inorganic cocatalyst is a cobalt(II) complex with bis[3-(salicylalamino)propyl]methylamine, said complex hereinafter being designated "CoSMDPT".

Suitable organic cocatalysts include various terpyridine, phenanthroline, quinoline and isoquinoline compounds including 2,2':6',2"-terpyridine, 4'-methylthio-2,2':6',2"-terpyridine and 2,2':6',2"-terpyridine N-oxide, 1,10-phenanthroline, 2,4,7,8-tetramethyl-1,10-phenanthroline, 4,7-diphenyl-1,10,phenanthroline and 3,4,7,8-tetramethyl-1,10-phenanthroline. The terpyridines and especially 2,2':6',2"-terpyridine are generally preferred.

The chloride or bromide, preferably bromide, source employed according to the present invention is a hexaalkylguanidinium chloride or bromide of the type disclosed in U.S. Pat. No. 5,229,482, the disclosure of which is incorporated by reference herein. Included are the α,ω-bis(pentaalkylguanidinium)alkane salts. Salts in which the alkyl groups contain 2-6 carbon atoms are preferred, with hexaethylguanidinium bromide being especially preferred.

The proportion of Group VIIIB metal source employed is an amount sufficient to provide about 1 gram-atom of metal per 800–10,000 and preferably 2,000–5,000 moles of hydroxyaromatic compound. For each gram-atom of Group VIIIB metal there is usually employed about 0.1–5.0 and especially about 0.5–1.5 gram-atoms of cobalt, about 0.1–3.0 and preferably about 0.3–1.0 moles of organic cocatalyst and about 2–150, preferably about 5–40, moles of hexaalkylguanidinium halide.

Gas is supplied to the reaction mixture in proportions of about 2–50 mole percent oxygen, with the balance being carbon monoxide. The gases may be introduced separately or as a mixture, to a total pressure in the range of about 10–250 atmospheres. Reaction temperatures in the range of about 60–150° C. are typical. Drying agents, typically molecular sieves, may be present in the reaction vessel. In order for the reaction to be as rapid as possible, it is preferred to maintain the reaction pressure in accordance with the aforementioned U.S. Pat. No. 5,399,734 until conversion of the hydroxyaromatic compound is complete.

The diaryl carbonates produced by the method of this invention may be isolated by conventional techniques. It is often preferred to form and thermally crack an adduct of the diaryl carbonate with the hydroxyaromatic compound, as described in U.S. Pat. Nos. 5,239,106 and 5,312,955.

The invention is illustrated by the following examples.

EXAMPLE 1

A constant composition gas flow reactor system, as disclosed in the aforementioned U.S. Pat. No. 5,399,734, was charged with 61.94 g (658 mmol) of phenol, 990.1 mg (3.21 mmol) of hexaethylguanidinium bromide, 123.3 mg (0.300 mmol) of CoSMDPT, 23.6 mg (0.101 mmol) of 2,2':6',2"-terpyridine and 67.5 mg (0.293 mmol) of palladium(II) acetate. Molecular sieves, 41 g, were placed in a perforated polytetrafluoroethylene basket mounted to the stir shaft of the reactor.

The reactor was sealed and heated to 110° C., with stirring, and a mixture of 9.5 mole percent oxygen and 91.5 mole percent carbon monoxide was introduced at a flow rate of 344 ml/min and a pressure of about 41 atmospheres. Gas flow was continued for 2 hours, after which a portion of the reaction mixture was removed and analyzed by high pressure liquid chromatography. The yield of diphenyl carbonate was found to be 42%, and the selectivity to diphenyl carbonate was 94%.

In a control reaction, run under identical conditions using an essentially equivalent amount of tetra-n-butylammonium bromide in place of the hexaalkylguanidinium bromide, the yield of diphenyl carbonate was 38% with a selectivity to diphenyl carbonate of 94%. Thus, the method of this invention afforded diphenyl carbonate in higher yield without a loss in selectivity.

EXAMPLE 2

The procedure of Example 1 was repeated, substituting palladium(II) 2,4-pentanedioate for the palladium(II) acetate. The yield of diphenyl carbonate was 38%, and the selectivity was 85%. In the control, the yield was 35% and the selectivity 85%, This again shows the yield advantage provided by the method of the invention.

What is claimed is:

1. A method for preparing a diaryl carbonate which comprises contacting at least one hydroxyaromatic compound with oxygen and carbon monoxide in the presence of an amount effective for carbonylation of at least one catalytic material including an effective proportion of a source of bromide or chloride, said source being at least one hexaalkylguanidinium bromide or chloride.

2. A method according to claim 1 wherein the catalytic material comprises palladium or a compound thereof, an inorganic cocatalyst and an organic cocatalyst.

3. A method according to claim 2 wherein the hydroxyaromatic compound is phenol.

4. A method according to claim 2 wherein the catalytic material comprises a palladium(II) salt of a $C_{2-6}$ aliphatic carboxylic acid.

5. A method according to claim 4 wherein the palladium (II) salt is palladium(II) acetate.

6. A method according to claim 2 wherein the catalytic material comprises a palladium(II) salt of a β-diketone.

7. A method according to claim 6 wherein the palladium (II) salt is palladium(II) 2,4-pentanedionate.

8. A method according to claim 2 wherein the inorganic cocatalyst is a cobalt(II) salt with an organic compound capable of forming a pentadentate complex.

9. A method according to claim 8 wherein the organic compound is bis[3-(salicylalamino)propyl]methylamine.

10. A method according to claim 2 wherein the organic cocatalyst is a terpyridine, phenanthroline, quinoline or isoquinoline compound.

11. A method according to claim 10 wherein the organic cocatalyst is 2,2':6',2"-terpyridine.

12. A method according to claim 2 wherein the alkyl groups in the hexaalkylguanidinium salt contain 2–6 carbon atoms.

13. A method according to claim 12 wherein the source is a hexaalkylguanidinium bromide.

14. A method according to claim 13 wherein the hexaalkylguanidinium bromide is hexaethylguanidinium bromide.

15. A method according to claim 2 wherein the proportions of oxygen and carbon monoxide are about 2–50 mole percent oxygen, with the balance being carbon monoxide.

16. A method according to claim 2 wherein the proportion of palladium is about 1 gram-atom per 2,000–5,000 moles of hydroxyaromatic compound.

17. A method according to claim 16 wherein about 0.5–1.5 gram-atoms of cobalt, about 0.3–1.0 mole of organic cocatalyst and about 20–50 moles of hexaalkylguanidinium halide are employed per gram-atom of palladium.

* * * * *